United States Patent
Chiavone et al.

(10) Patent No.: US 9,383,300 B2
(45) Date of Patent: Jul. 5, 2016

(54) PRECISION CONVECTION SYSTEM

(71) Applicant: Akrometrix Inc., Atlanta, GA (US)

(72) Inventors: Ken Chiavone, Statham, GA (US); Joseph Gheesling, Lilburn, GA (US)

(73) Assignee: Akrometrix Inc., Atlanta, GA (US)

( * ) Notice: Subject to any disclaimer, the term of this patent is extended or adjusted under 35 U.S.C. 154(b) by 0 days.

(21) Appl. No.: 14/656,017

(22) Filed: Mar. 12, 2015

(65) Prior Publication Data
US 2015/0268143 A1    Sep. 24, 2015

Related U.S. Application Data

(60) Provisional application No. 61/955,364, filed on Mar. 19, 2014.

(51) Int. Cl.
| | |
|---|---|
| *G01N 21/00* | (2006.01) |
| *G01N 1/44* | (2006.01) |
| *G01B 11/02* | (2006.01) |
| *G01B 11/25* | (2006.01) |
| *G01N 21/03* | (2006.01) |
| *G01N 25/16* | (2006.01) |

(52) U.S. Cl.
CPC ........ *G01N 1/44* (2013.01); *G01B 11/02* (2013.01); *G01B 11/254* (2013.01); *G01N 21/03* (2013.01); *G01N 25/16* (2013.01)

(58) Field of Classification Search
CPC .......... G01N 2035/00326; G01N 2035/00495; G01N 35/026; G01N 35/00871; G01N 35/10; G01N 15/1475; G01N 2015/008; G01N 2015/1486; G01N 2035/00356; G01N 2035/00366; G01N 2035/00425; G01N 2035/0449
See application file for complete search history.

(56) References Cited

U.S. PATENT DOCUMENTS

| | | | | |
|---|---|---|---|---|
| 5,182,231 | A * | 1/1993 | Hongo | H01L 21/76892 257/E21.595 |
| 5,971,249 | A * | 10/1999 | Berkin | B23K 1/008 228/102 |
| 5,984,524 | A * | 11/1999 | Teshirogi | G01B 11/16 374/5 |
| 6,168,064 | B1 * | 1/2001 | Berkin | B23K 1/008 219/388 |
| 6,564,166 | B1 * | 5/2003 | Ume | G01B 11/25 702/136 |
| 6,714,300 | B1 * | 3/2004 | Rosencwaig | G01N 21/211 257/E21.226 |
| 2002/0146657 | A1 * | 10/2002 | Anderson | B23K 1/008 432/11 |
| 2003/0045098 | A1 * | 3/2003 | Verhaverbeke | H01L 21/67069 438/689 |
| 2006/0279311 | A1 * | 12/2006 | Steeples | G01R 31/311 324/750.03 |
| 2011/0248068 | A1 * | 10/2011 | Ohtashiro | B23K 1/0016 228/10 |
| 2012/0162640 | A1 * | 6/2012 | Sakagami | G01N 21/658 356/301 |
| 2015/0268143 | A1 * | 9/2015 | Chiavone | G01N 1/44 356/244 |

* cited by examiner

*Primary Examiner* — Michael P Stafira
(74) *Attorney, Agent, or Firm* — King & Spalding

(57) ABSTRACT

A system can use light to analyze a sample dimensionally, for example via shadow moiré analysis. The system can apply convection to heat the sample during analysis. A platform of the system can support the sample during convection-based heating. The system can include nozzles that are arranged circumferentially about the platform. The nozzles can have openings oriented towards the platform to emit heated air towards the sample, to heat the sample. Members such as fins or posts within each nozzle can diffuse or spread the emitted air.

2 Claims, 10 Drawing Sheets

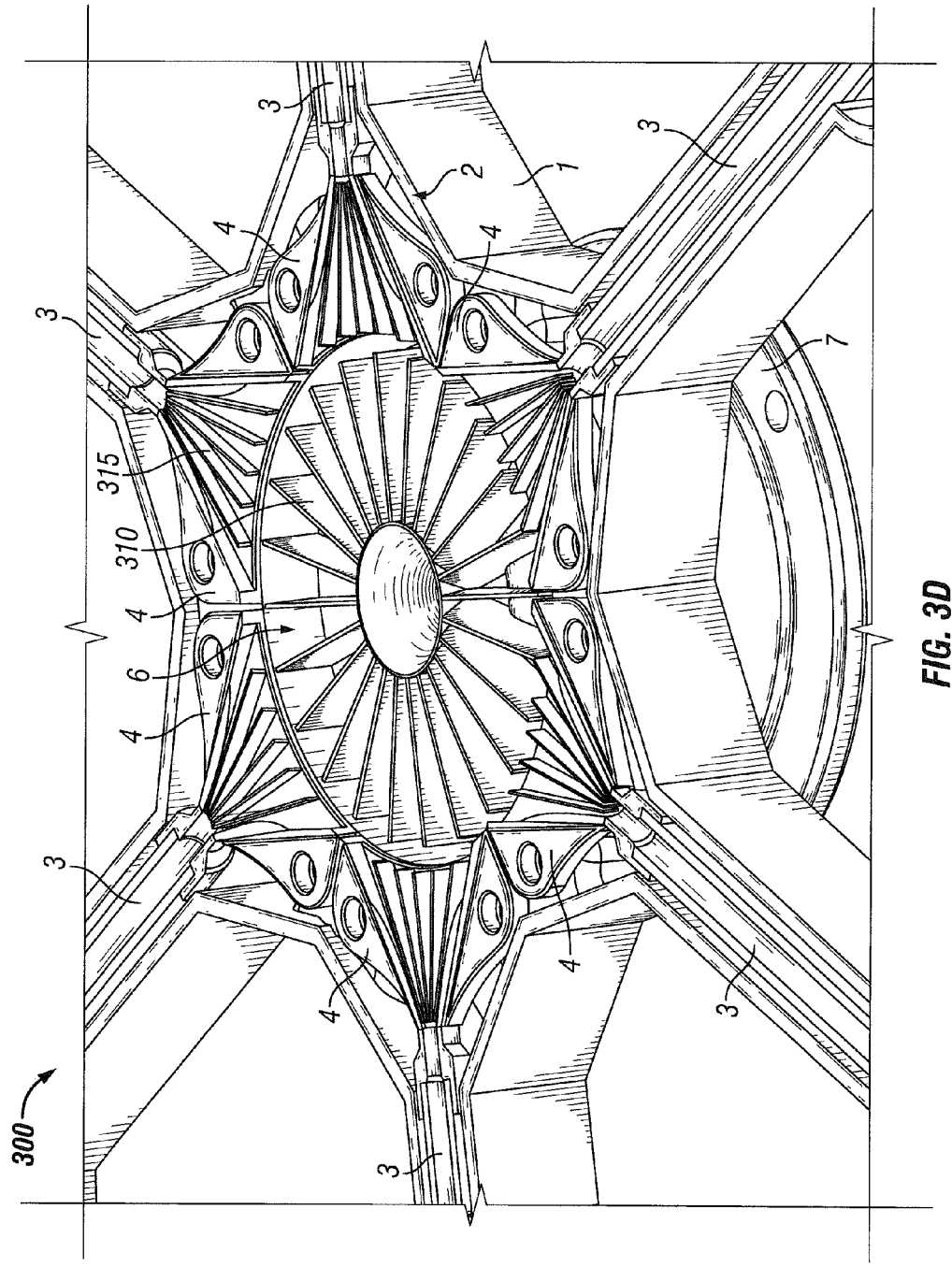

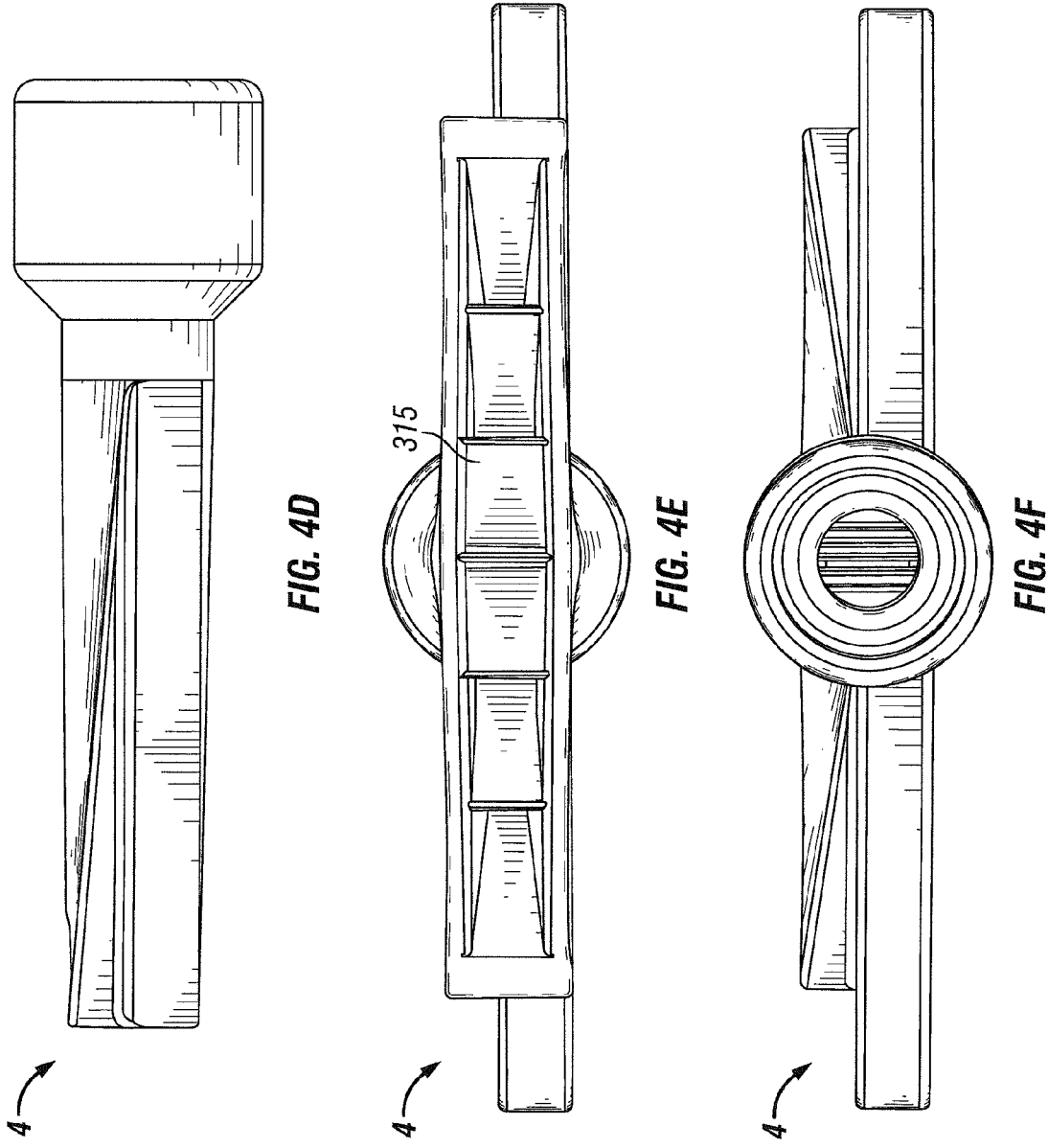

PRECISION CONVECTION SYSTEM

CROSS REFERENCE TO RELATED APPLICATIONS

This application claims priority to U.S. Provisional Patent Application No. 61/955,364 filed Mar. 19, 2014 in the name of Ken Chiavone and Joseph Gheesling and entitled "Precision Convection System," the entire disclosure of which is hereby incorporated herein by reference.

TECHNICAL FIELD

Embodiments of the disclosure relate generally to precision convection, and more particularly to a system for precisely controlling temperature of a sample to facilitate using optics to take dimensional measurements of the sample.

BACKGROUND

Modern computing and communication devices incorporate electronic systems such as chips, hybrids, microprocessors, connectors, and miniature circuit boards, to mention a few representative examples. The circuitry of these electronic systems typically utilizes many different materials, structures, and components that have substantially different thermal expansion properties. Manufacture often involves a reflow process in which the circuitry is heated to a sufficient temperature to produce solder flow.

In the heating process, the circuitry's different materials expand differently, resulting in strains and stresses that can negatively impact reliability if not properly taken into account during circuit design. For example, polymers, composites, metals, glasses, films, and ceramics in the circuitry can expand at different rates when heated during reflow and can contract differently during subsequent cooling.

Engineers may model and attempt to account for the different thermal expansion characteristics of the circuitry elements during design. However, there is typically deviation between conventional models and the actual performance during mass production reflow. Some of this deviation may be due to a conventional model's inability to account fully for the way the circuitry is heated during mass production. When the deviation between modeled and actual performance is sufficiently large to cause a reliability issue, the circuit design typically needs to be modified. However, redesigning a circuit after the circuit is in mass production can cause product release delays and substantial expense. Accordingly, circuit designers need information early in the design process about how their designs will behave in the thermal environment and operating conditions of a mass production reflow process.

For example, technology is needed for emulating parameters or conditions of a circuitry heating process of a mass production reflow process. Need exists for simulating heating and mechanical results associated with a reflow process. Need exists for a system that can heat a sample, such as an electronic system or circuitry or some other device, precisely. Need exists for a system that can heat a sample uniformly. Need exists for a system that can heat a sample using convection. Need exists for a system that can provide or facilitate dimensional measurements of a sample while the sample is being precisely heated, for example under conditions emulating a reflow process.

There is further need in the art for an improved approach to heating samples while measuring them optically, such as with high-resolution shadow moiré technology, to better simulate what happens in a production reflow oven. There is further need in the art for a means to heat a sample in a confined space, such as when a physical glass grating of a shadow moiré instrument is located adjacent a measured surface. A capability addressing one or more such needs, or some other related deficiency in the art, would support better heating, modeling, and metrology.

SUMMARY

In one aspect of the disclosure, a system can heat or thermally control or manipulate a sample precisely to facilitate taking dimensional measurements of the sample using light. The system can comprise a platform that supports the sample. The system can apply heat to the sample using hot air delivered from one or more nozzles that diffuse the hot air. The nozzle or nozzles can be pointed towards the platform or the sample, for example likes spokes pointed inwards towards a hub of a wheel.

The foregoing discussion of heating samples is for illustrative purposes only. Various aspects of the present technology may be more clearly understood and appreciated from a review of the following text and by reference to the associated drawings and the claims that follow. Other aspects, systems, methods, features, advantages, and objects of the present technology will become apparent to one with skill in the art upon examination of the following drawings and text. It is intended that all such aspects, systems, methods, features, advantages, and objects are to be included within this description and covered by this application and by the appended claims of the application.

BRIEF DESCRIPTION OF THE DRAWINGS

FIGS. 3A, 3B, 3C, and 3D (collectively FIG. 3) respectively illustrate a perspective view, an exploded view, a cross sectional perspective view, and a detail cross sectional perspective view of a convection system that may be deployed in a radiant oven according to some example embodiments of the present disclosure.

FIGS. 4A, 4B, 4C, 4D, 4E, and 4F (collectively FIG. 4) illustrate five views of a nozzle for a convection system according to some example embodiments of the present disclosure.

Figure 1A:
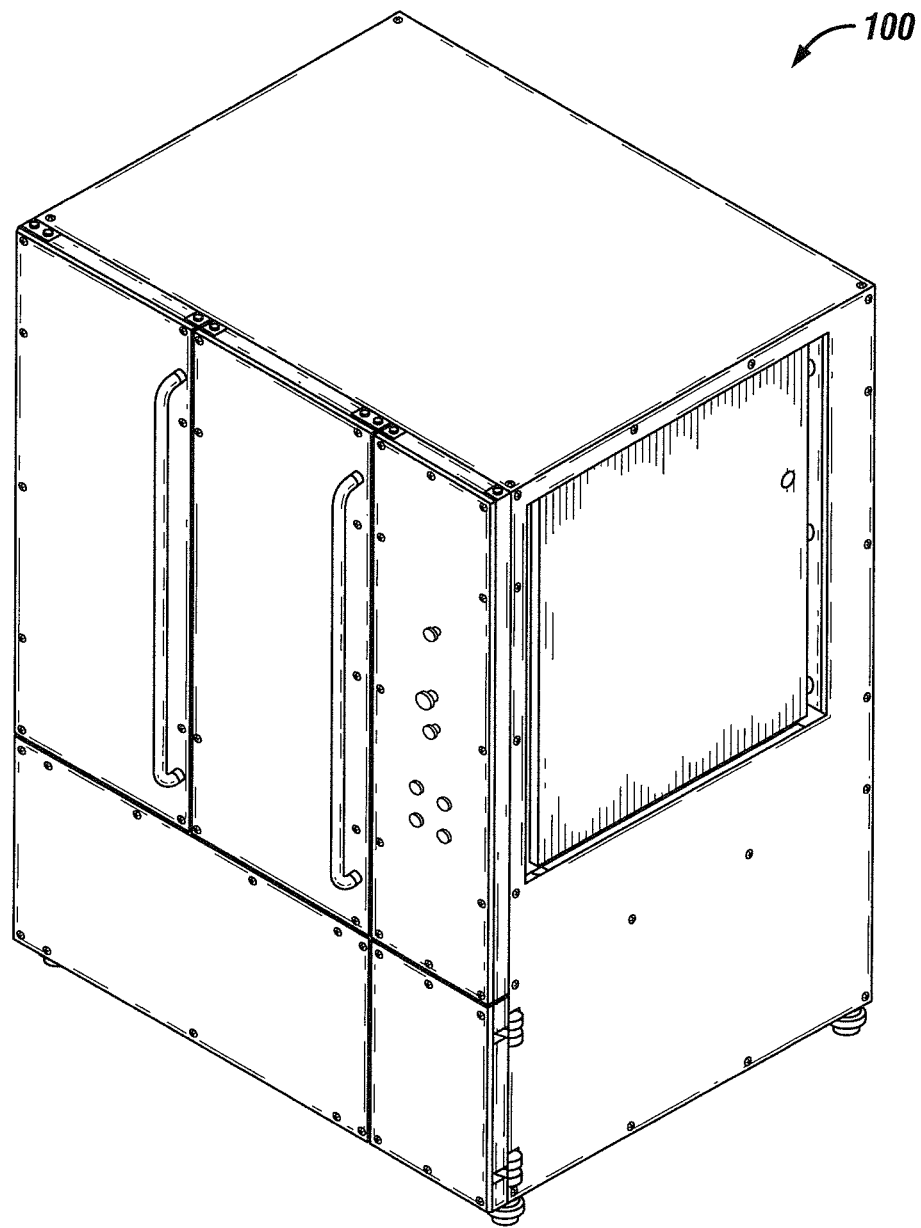
FIGS. 1A and 1B (collectively FIG. 1) respectively illustrate perspective and exploded views of an optical metrology system according to some example embodiments of the present disclosure.

The drawings illustrate only example embodiments and are therefore not to be considered limiting of the embodiments described, as other equally effective embodiments are within the scope and spirit of this disclosure. The elements and features shown in the drawings are not necessarily drawn to scale, emphasis instead being placed upon clearly illustrating principles of the embodiments. Additionally, certain dimensions or positioning may be exaggerated to help visually convey certain principles. In the drawings, similar reference numerals among different figures designate like or corresponding, but not necessarily identical, elements.

DESCRIPTION OF EXAMPLE EMBODIMENTS

A convection system can precisely apply heat to a sample while the sample undergoes optical metrology. In some example embodiments, the sample can comprise circuitry that is to be produced via a solder reflow process, for example a miniature circuit board or other circuit element for a handheld computing or communication device. Chips, hybrids, microprocessors, miniature circuit boards, package-on-packages (PoPs), and sockets are a few other representative examples of samples comprising circuitry that may undergo the optical metrology. In some example embodiments, the applied heat can emulate conditions in the solder reflow process to predict mechanical performance in a production environment. In some embodiments, the optical metrology can utilize light to assess dimensional changes across the circuitry. In some embodiments, these dimensional changes can be caused by or associated with various materials of the circuitry expanding differently due to having different thermal expansion characteristics.

The present technology can be embodied in many different forms and should not be construed as limited to the embodiments set forth herein; rather, these embodiments are provided so that this disclosure will be thorough and complete, and will fully convey the scope of the technology to those having ordinary skill in the art. Furthermore, all "examples," "embodiments," "example embodiments," or "exemplary embodiments" given herein are intended to be non-limiting and among others supported by representations of the present technology.

Convection systems will now be described more fully with reference to FIGS. 1-5, which describe representative embodiments of the present technology. FIGS. 1 and 2 describe an example operating environment for a convection system, while FIGS. 3, 4, and 5 describe an example convection system.

Figure 1B:
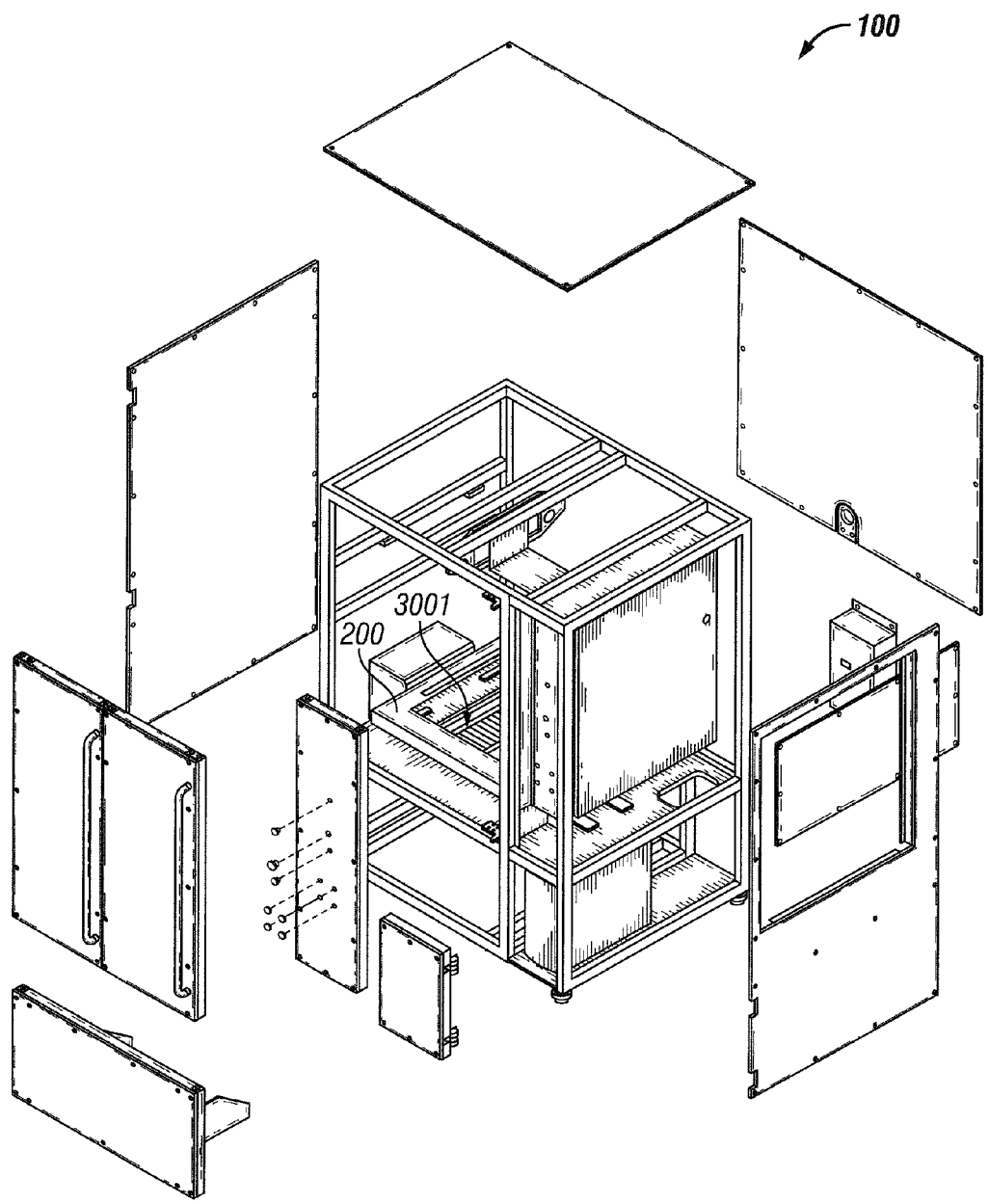
Figure 2C:
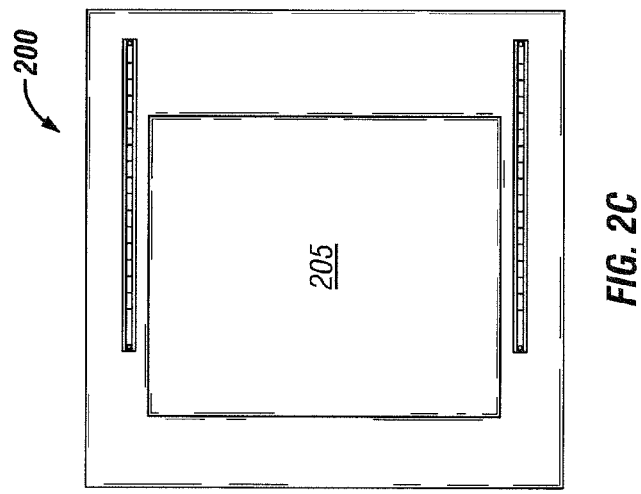
FIGS. 2A, 2B, and 2C (collectively FIG. 2) respectively illustrate perspective side and top views of a radiant oven that may be deployed in an optical metrology system according to some example embodiments of the present disclosure.
Figure 2A:
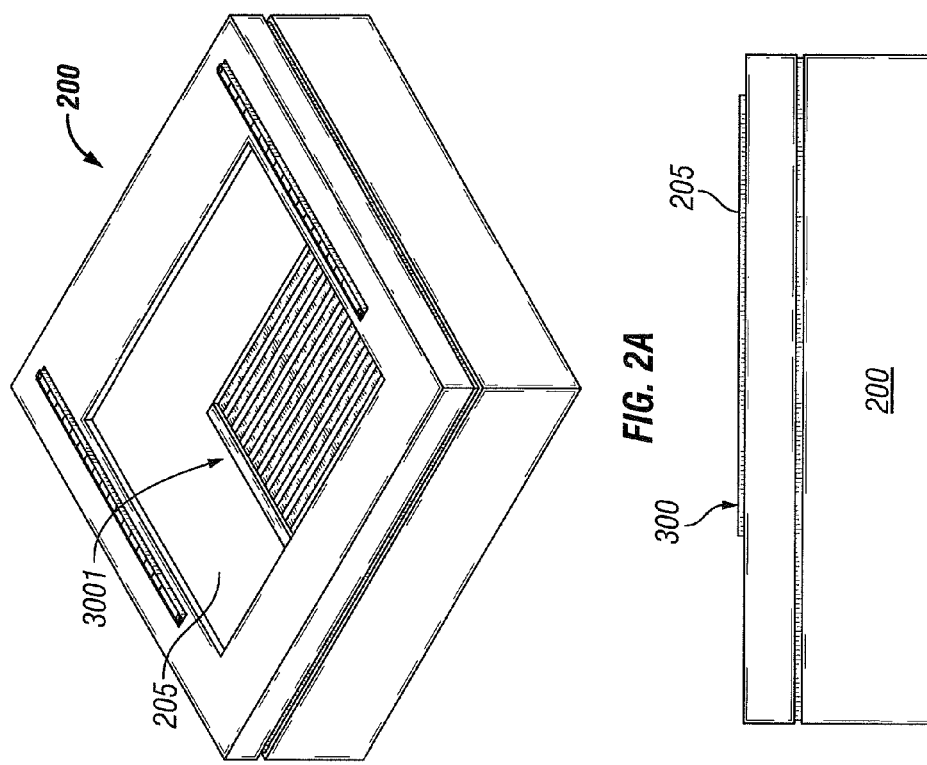
Figure 2B:
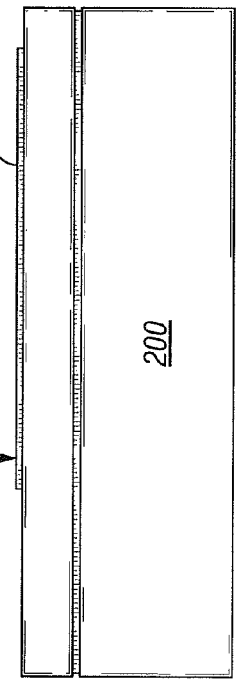

Turning now to FIG. 1, this figure illustrates an example optical metrology system 100 in accordance with some embodiments of the present disclosure. FIG. 1A illustrates a perspective view of the optical metrology system 100 in assembled form. FIG. 1B illustrates a perspective view of the optical metrology system 100 in exploded form.

In the illustrated example embodiment of FIG. 1, the optical metrology system 100 is configured for shadow moiré operation and comprises a shadow moiré instrument, as discussed below. However, various embodiments may perform other forms of optical based metrology. For instance, in some embodiments an optical metrology system in accordance with the present disclosure can practice laser or projection moiré, digital fringe projection (DFP), digital image correlation (DIC), laser triangulation, structured light projection measurements, or confocal microcopy, to mention a few representative examples without limitation.

As shown in FIG. 1B, the optical metrology system 100 houses a radiant oven 200, an example embodiment of which is illustrated in FIG. 2 and further discussed below. The radiant oven 200 provides an enclosed space 3001 to house a convection system 300 for sample heating, with an example embodiment of the convection system 300 illustrated in FIG. 3 and further discussed below. In one example embodiment, the optical metrology system 100 can comprise a system commercially available from Akrometrix, LLC of Atlanta, Ga. under the registered trade name THERMOIRE. In an example embodiment, the optical metrology system 100 is on the order of approximately six feet (183 cm) in height.

Shadow moiré technology-based measurement of the optical metrology system 100 is well suited for measuring circuitry dimensionally in a thermal environment, for example to understand mechanical behavior of circuitry in a simulated reflow chamber. Shadow moiré technology can provide a combination of high-precision measurement (for example a resolution of 1-2 microns in the measured direction) and a large field of view for that measurement (on the order of 400×400 mm or larger).

Shadow moiré typically utilizes a physical 'grating' of ruled lines placed close to a surface of a sample that is to be measured. The grating lines, called rulings, are typically spaced close together, such as at a frequency of 100 dark/light line pairs per inch. The rulings can be made of opaque metal compounds printed on a clear glass surface. Light shines through the grating, casting a set of line shadows on the surface to be measured. Viewed from above, an effect caused by optical physics is readily observed, called the moiré effect. The two patterns, the lines on the grating and the shadows below the grating, interfere optically to create a non-linear pattern that can be viewed and recorded by a camera. Capturing a set of these interference images and processing them with a computer program provides precise calculated data describing the relative heights of features on the surface being measured.

For best measurement accuracy, the ruled glass grating typically should be close to the surface being measured, for example within about 6 mm or so for some gratings. Accordingly, there may be physical constraints associated with using a physical glass grating above the surface being measured.

The confines of this sized-constrained area can impose challenges on heating the sample using conventional heating technologies. The proximity of the relatively cool glass grating to the surface of the sample undergoing metrology can create temperature gradients difficult to overcome with gross circulation of air throughout the internal volume of the optical metrology system 100. There is typically inadequate room between the glass and the measured sample for such gross air circulation to achieve uniform heating across the sample.

However, the optical metrology system 100 can incorporate the convection system 400 to heat the sample uniformly or precisely in this cramped area. Moreover, embodiments in accordance with the figures can simulate conditions of a production reflow oven so that design engineers can accurately predict thermal performance of circuitry prior to volume production.

When electronics are assembled in a production reflow oven, fast moving forced hot air is typically circulated in a closed chamber as circuit assemblies progress through the oven on a moving belt or chain. Thermodynamically, the heat transfer is nearly optimal, since the assemblies are exposed to hot air of a relatively uniform temperature. Using the optical metrology system 100 with the radiant oven 200 and the convection system 300, engineers can measure components in their laboratory under simulated conditions of a production reflow environment, in order to understand how the components may change and warp during actual production assembly.

Turning now to FIG. 2, this figure illustrates the example radiant oven 200 in accordance with some embodiments of the present disclosure. As discussed above, the illustrated radiant oven 200 may be deployed in the optical metrology system 100 illustrated in FIG. 1. The illustrated radiant oven 200 provides an enclosed space 3001 to house the convection system 300 illustrated in FIG. 4, for example.

In the illustrated embodiment, the radiant oven 200 comprises a transparent lid 205 that opens and shuts for access to the enclosed space 3001. In an example embodiment, the transparent lid 205 comprises glass. The transparent lid 205 can comprise a window.

The transparent lid 205 transmits light to and from a sample, so that the sample can be dimensionally analyzed as discussed above. For example, a shadow moiré grating can be positioned under the transparent lid 205 for analysis of a sample located in the enclosed space 3001. A light source (not illustrated) can illuminate the grating and the sample through the transparent lid 205. A camera (not illustrated) mounted above the transparent lid 205 can record light transmitting from the sample, for example to capture shadow moiré images for dimensional analysis of the sample.

Figure 3A:
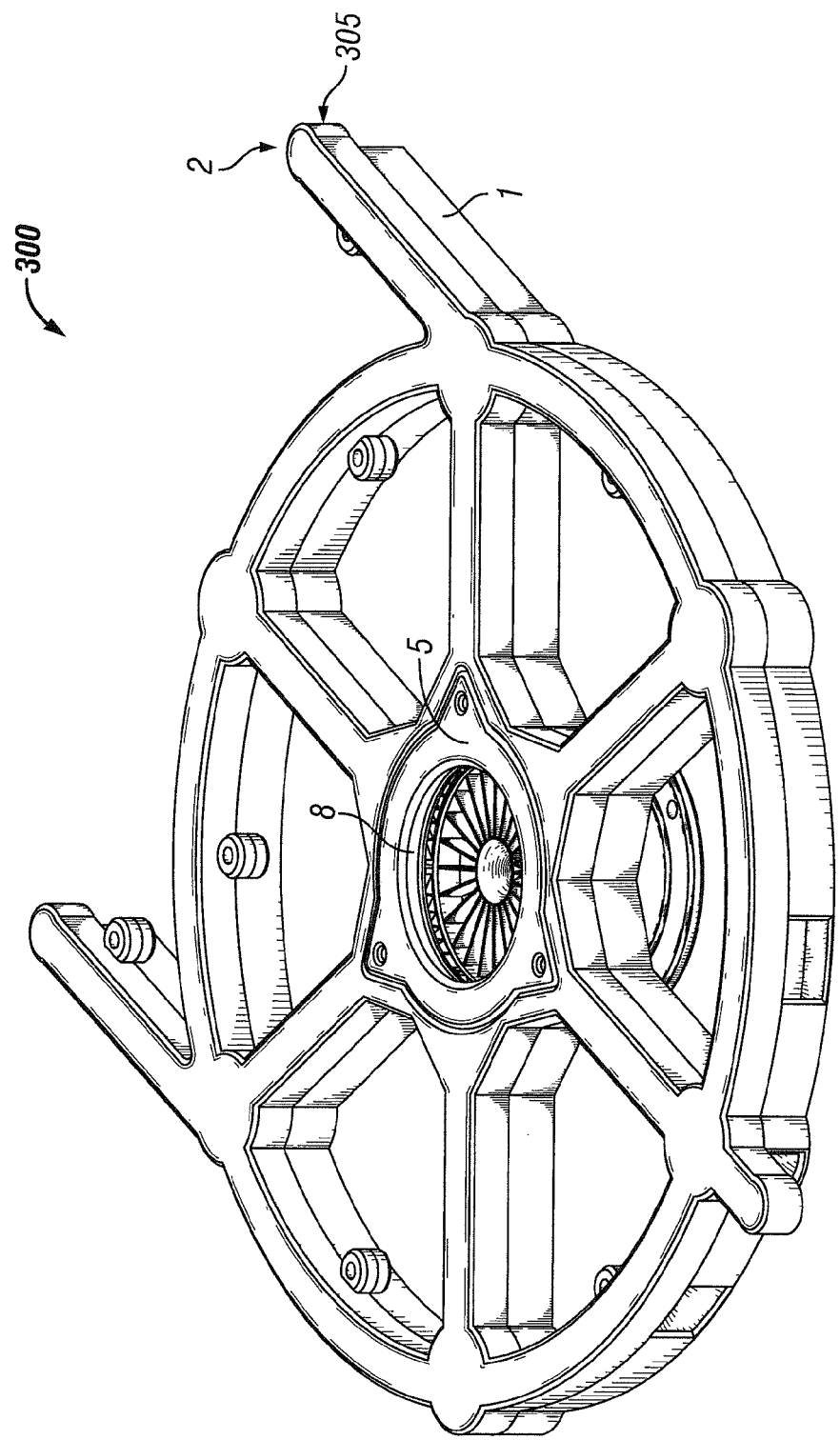
Figure 3B:
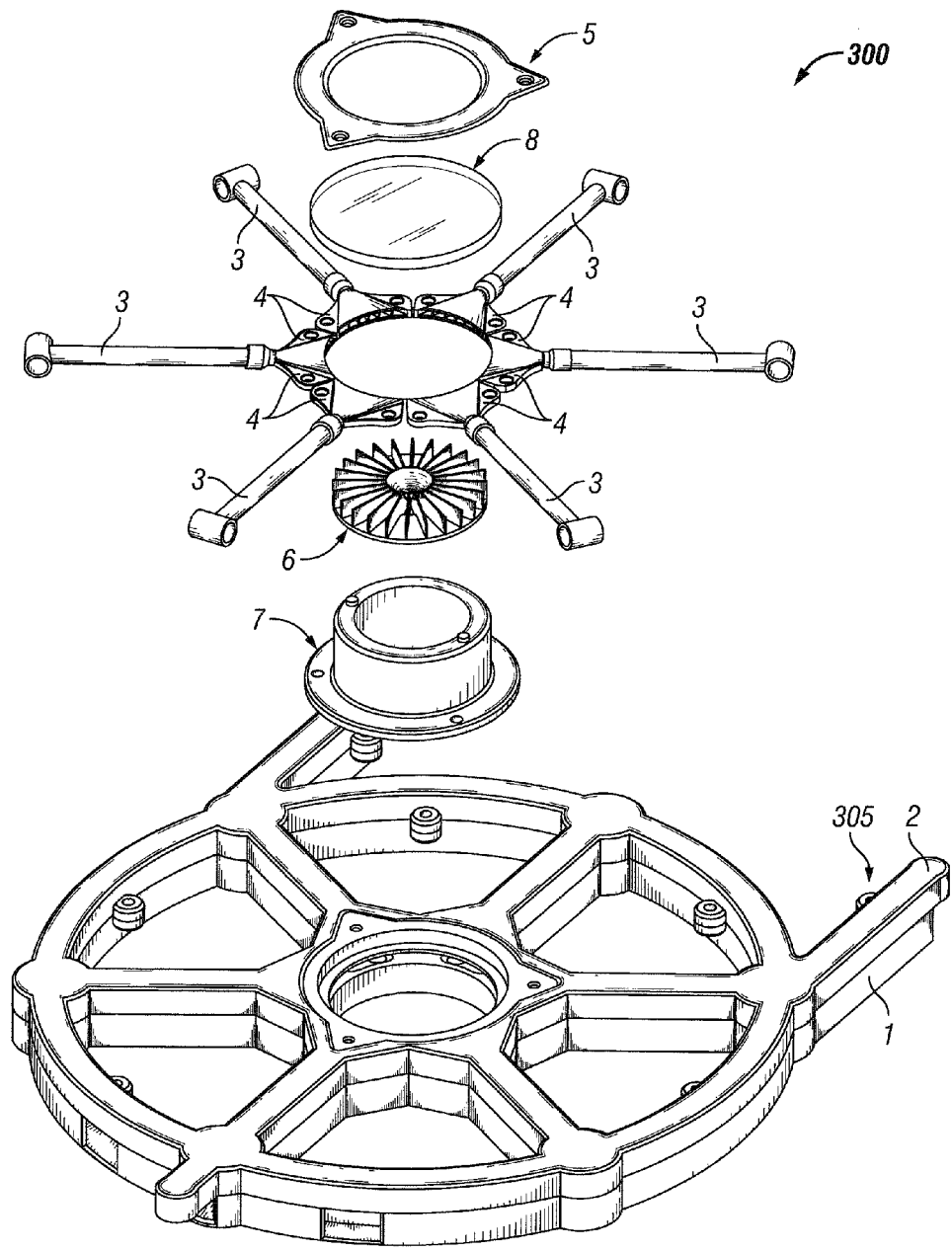
Figure 3C:
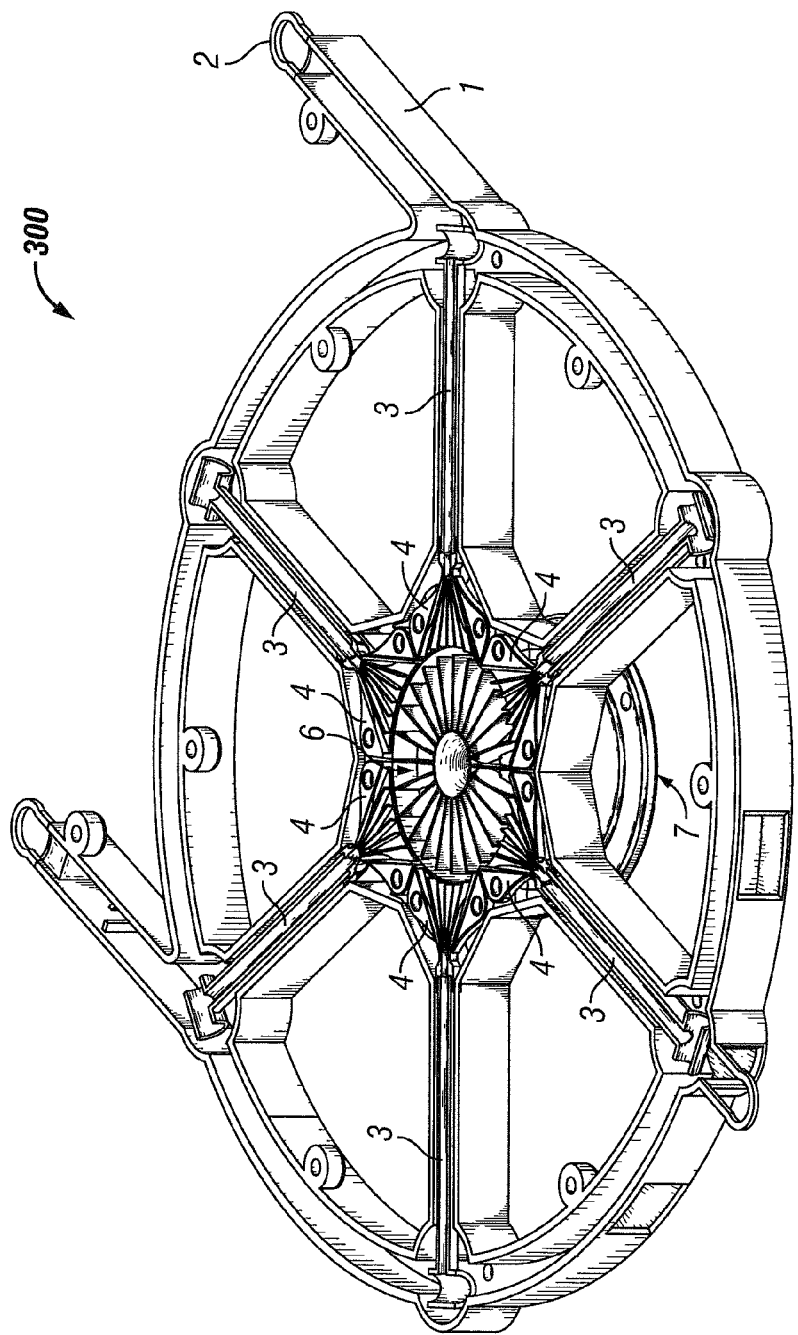

Turning now to FIG. 3, this figure illustrates an example convection system 300 in accordance with some embodiments of the present disclosure. FIG. 3A illustrates a perspective view of the convection system 300 as assembled. FIG. 3B illustrates a corresponding exploded view of the convection system 300, showing example components. FIG. 3C illustrates a perspective view of a cross section of the convection system 300, showing example internal features. FIG. 3D further illustrates a perspective view of the cross section of the convection system 300, specifically providing a magnified view detailing a central area of the convection system 300.

Accordingly, FIG. 3 illustrates representative components and structure for an exemplary embodiment of the convection system 300. The illustrated convection system 300 may be deployed in the radiant oven 200 illustrated in FIG. 2, for example. The convection system 300 can deliver benefits of convection-based heating in a representative scenario of measuring samples that are close to a glass surface.

In operation, compressed air is supplied to a manifold 305 that comprises an air channel having a circular form in the illustrated embodiment. The manifold 305 distributes the compressed air to air-heating channels 3 comprising electric heater tubes. As the compressed air flows through the air-heating channels 3, the electric heater tubes heat the air. The resulting heated air exits the air-heating channels 3 through nozzles 4 that are arranged to circumscribe a platform 310, with the platform 310 supporting the sample undergoing optical metrology. The heated air raises the temperature of the sample uniformly through precise convection.

In the illustrated example embodiment, the convection system 300 is arranged in a hub-and-spokes geometry, where the platform 310 is located as a hub of the geometry, the air-heating channels 3 are located as spokes of the geometry, and manifold 305 is located as an outer rim of the geometry.

The manifold 305 comprises an upper shell 2 and a lower shell 1. The upper shell 2 and the lower shell 1 can fit together and be fastened to one another using screws, bonding, welding, a gasket, rivets, epoxy, or some other appropriate fastening or sealing means. In an example embodiment, the upper and lower shells 2, 1 can be comprised of cast metal or other appropriate material.

A base 7 supports the convection system 300. The base 7 may be mounted or otherwise positioned inside the radiant oven 200, for example by fastening to an interior surface of the radiant oven's housing.

A window 8 transmits light two and from a sample (not illustrated) resting on the platform 6. The window 8 is held in place by an example retention ring 5 that circumscribes the window 8. In an example embodiment, the window 8 comprises a shadow moiré grating as discussed above.

The sample undergoing optical metrology (for example using shadow moiré or other appropriate light-based dimensional analysis) is located in a narrow space between the platform 6 and the window 8. A mechanism (not illustrated) within the radiant oven 200 can raise and lower the platform to a user-defined height beneath the interior surface of the window 8. In some embodiments, the mechanism can comprise a computer-controlled servo, for example. Thus, the sample is readily positioned in a centrally located pocket of air below the window 8.

To achieve uniform sample heating, the nozzles 4 are arranged to extend about the periphery of the platform 6 and are pointed inward, towards the platform 6 and the sample. In this example arrangement, the nozzles 4 distribute hot air evenly inside the central air pocket where the sample to be measured is positioned. The resulting uniform temperature control of the sample can simulate conditions of a production reflow environment, for example.

When convection cooling is desired, the heater tubes of the air-heating channels 3 can be de-energized. Cooler air passing through the nozzles 4 can uniformly cool the samples back to room temperature. Accordingly, sample temperature can be precisely increased, maintained, decreased, or cycled, including before, during, or after optical metrology.

In various embodiments, the convection system 300 can be computer controlled. For example, a software routine can vary raise or lower the platform 6 at various times during a reflow simulation. As another example, a software routine can automatically manipulate sample temperature by adjusting airflow temperature to simulate a reflow temperature cycle, for example. As another example, a software routine can adjust airflow through individual nozzles 4 or system-wide by controlling electromechanical air valves, for example.

Turning now to FIG. 4, this figure illustrates an example nozzle 4 for the convection system 300 in accordance with some embodiments of the present disclosure.

Figure 4A:
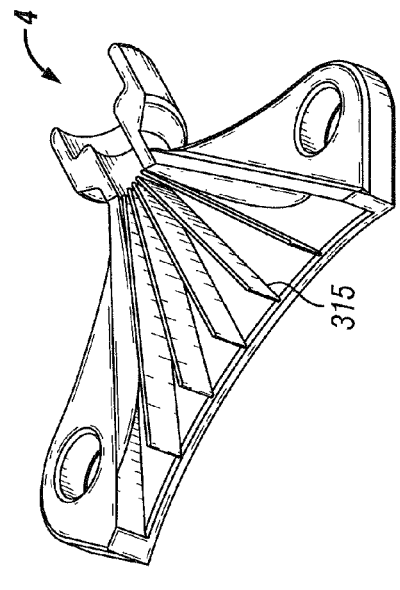
Figure 4B:
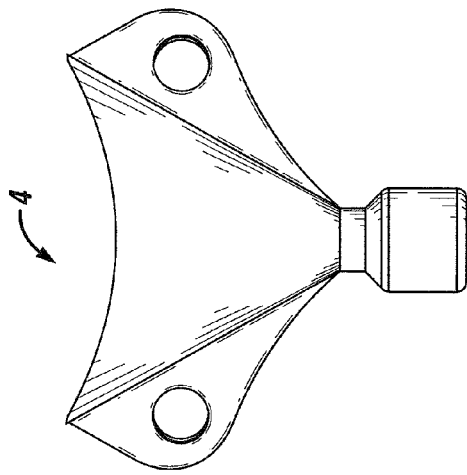
Figure 4C:
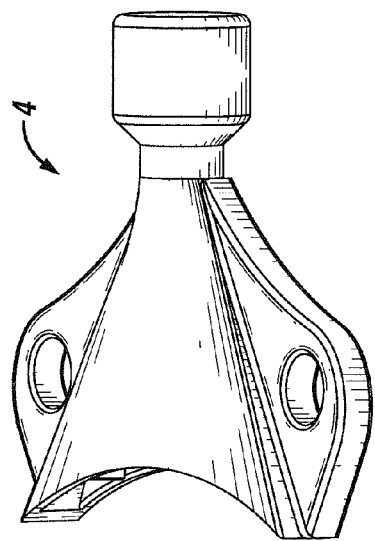
Figure 5A:
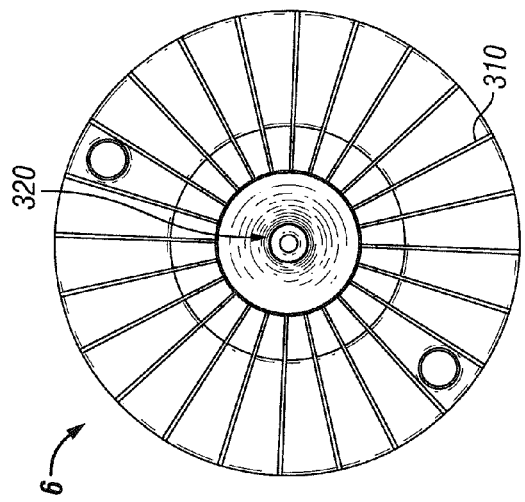
FIGS. 5A, 5B, 5C, and 5D (collectively FIG. 5) illustrate perspective, top, bottom, and side views of sample platform for a convection system according to some example embodiments of the present disclosure.
Figure 5B:
Figure 5C:
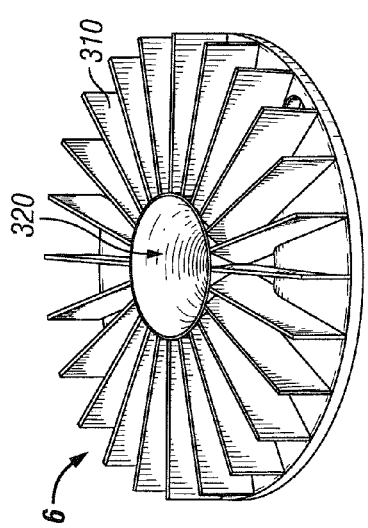
Figure 5D:
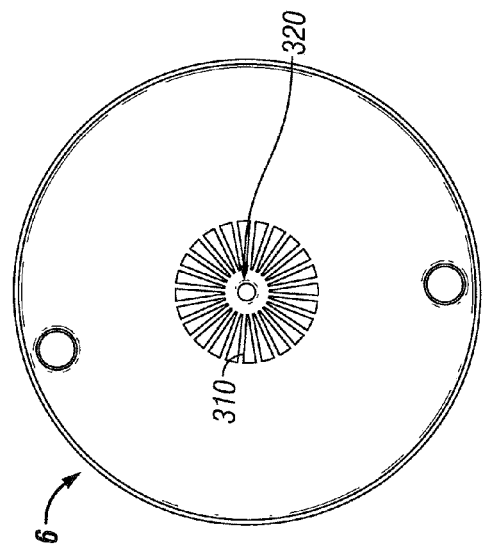

FIG. 4A illustrates a perspective view. FIG. 4B illustrates a cross sectional view in perspective. FIG. 4C illustrates a top view. FIG. 4D illustrates a side view. FIG. 4E illustrates a front view. FIG. 4F illustrates a rear view.

In the illustrated embodiment, each nozzle 4 flattens out, diffuses, and spreads the air passing through the air-heating channels. The nozzles 4 thus control how the exiting air will move into the air pocket where the sample to be measured is positioned.

As illustrated, each nozzle 4 has an outlet that is curved according to the periphery of the platform 6. Thus, the nozzles 4 and the platform 6 have matching contours facing one another in the illustrated embodiment.

Each nozzle 4 includes internal members 315 that extend across the airflow to diffuse or spread the air exiting the nozzle 4, further supporting uniform air distribution around the sample. In some embodiments, the internal members 315 can comprise vanes. In some embodiments, the internal members 315 can comprise posts or other structures that may interrupt, breakup, or otherwise control or manipulate the airflow.

In some example embodiments, the nozzles 4 maybe subjected to hot air at temperatures greater than 300 degrees Centigrade during normal operation. In some embodiments, each nozzle 4 is a single, solid piece of metal, for example stainless steel. Each nozzle 4 may be formed of a unitary piece of metal to be seamless. Other embodiments may be fabricated in two sections that are joined together via welding, screws, brazing, fusion, or other appropriate fastening means. In some example embodiments, each nozzle 4 can be made using 3D printing technology, for example laser sintering.

In some example embodiments, each nozzle 4 outputs heated air directly onto the platform 6. In some example embodiments, each nozzle 4 outputs heated air directly onto the sample. In some example embodiments, each nozzle 4 outputs a portion of heated air directly onto the platform 6 and another portion of heated air directly onto the sample.

Various embodiments of the nozzles 4 can comprise thinner outlet dimensions and different sizes, number, and shapes of the internal members 315, to mention a few representative variations that may be suited to different measurement applications, without limitation.

FIG. 4 illustrates an embodiment that incorporates six nozzles 4. Some embodiments may incorporate fewer or more nozzles 4 as may be suited to different applications or situations. Some embodiments may utilize a single nozzle, for example. Other embodiments may utilize two or more nozzles, for example. Accordingly, various embodiments may have different shapes, sizes, and numbers of nozzles.

In some embodiments, the nozzles 4 are positioned at a common height. In some embodiments, the nozzles 4 are positioned at staggered or otherwise different heights or distances below the window 8.

Turning now to FIG. 5, this figure illustrates an example sample platform 6 for the convection system 300 in accordance with some embodiments of the present disclosure. FIG. 5A illustrates a perspective view. FIG. 5B illustrates a top view. FIG. 5C illustrates a bottom view. FIG. 5D illustrates a side view.

In the illustrated embodiment, the sample platform 6 comprises vanes 310 radiating outward from a central opening 320. The vanes 310 form channels, between adjacent vanes 310, through which air can flow and diffusely exit the channels. The resulting airflow can produce uniform sample heating.

Accordingly, the vanes 310 can control and direct air exiting from the nozzles 4 as the air moves through the air pocket of the convection system 300 that is between the window 8 and the platform 6. In the illustrated embodiment, the vanes 310 comprise raised features of thin-wall metal and may be viewed as fins.

While illustrated in FIG. 5 as symmetrically radiating from the central opening 320, other embodiments may have a symmetry that corresponds to the number of nozzles 4. For example in some embodiments, the vanes 310 are arranged in a 3-way symmetry, and the convection system 300 has three nozzles 4 that are offset from each other by 120 degrees.

In the illustrated embodiment, a sample to be measured sits on top of the platform 6 and maybe supported by the vanes 310. In some embodiments, the upper portion of the vanes are beveled or pointed to reduce contact with the sample and to promote airflow around the sample.

In some example embodiments, the vanes 310 of the platform 6 are aligned circumferentially with the vanes 315 of the nozzles 4. In some example embodiments, the outlets of the nozzles 4 are slightly below the upper edges of the vanes 310. In some example embodiments, the outlets of the nozzles 4 are slightly above the upper edges of the vanes 310. In some example embodiments, the outlet of a single nozzle 4 is partially above and partially below the upper edges of the vanes 310.

In some example embodiments, the platform 6 can manufactured using direct metal laser sintering. For example, the vanes 310 can be build up layer-by-layer from melted steel powder, resulting in thin vanes 310 that may be relatively close together.

In various embodiments, the space between the platform 6 and the window 8 can be relatively large or small or may be sized to receive circuitry of various dimensions. In some embodiments, the space has an area no the order of at least 150×150 mm, for example. In some example embodiments, the space is generally circular in form. In some embodiments, the space has a form that may be square, octagonal, hexagonal, triangular, or some other appropriate geometry without limitation, for example. The space may further be configured with different heights according to sample size, for example. Thus, various air pocket sizes, shapes, and configurations are supported.

Technology for precision convection has been described. From the description, it will be appreciated that embodiments of the present technology overcome limitations of the prior art. Those skilled in the art will appreciate that the present technology is not limited to any specifically discussed application or implementation and that the embodiments described herein are illustrative and not restrictive. From the description of the example embodiments, equivalents of the elements shown therein will suggest themselves to those skilled in the art, and ways of constructing other embodiments of the present technology will appear to practitioners of the art.

What is claimed is:

1. A system comprising:
   a platform comprising:
      an upper side that comprises a central portion and a periphery; and
      a plurality of vanes that are disposed on the upper side and that radiate outward from the central area of the upper side towards the periphery of the upper side;
   a plurality of nozzles disposed about the periphery, each nozzle comprising:
      an outlet facing towards the central portion; and
      a plurality of members that are disposed in each nozzle and that are operative to spread heated air flowing out of the outlet;
   a first air channel extending circumferentially about the plurality of nozzles;
   a plurality of second air channels, each second air channel extending between the first air channel and a respective nozzle in the plurality of nozzles, each second air channel comprising a heater;
   a shadow moiré grating disposed adjacent the upper side of the platform; and
   a separation between the shadow moiré grating and the upper side of the platform, the separation sized for receiving a circuit to undergo dimensional testing.

2. The system of claim 1, wherein the plurality of members comprise a plurality of fins, and
   wherein the outlet is curved about the periphery.

* * * * *